US00PP31895P2

(12) United States Plant Patent
Bourne

(10) Patent No.: US PP31,895 P2
(45) Date of Patent: Jun. 23, 2020

(54) GRAPEVINE NAMED 'SV30-14-12'

(50) Latin Name: *Vitis vinifera*
Varietal Denomination: SV30-14-12

(71) Applicant: Sunview Vineyards of California, Inc, Delano, CA (US)

(72) Inventor: Timothy F. Bourne, Visalia, CA (US)

( * ) Notice: Subject to any disclaimer, the term of this patent is extended or adjusted under 35 U.S.C. 154(b) by 0 days.

(21) Appl. No.: 16/350,598

(22) Filed: Dec. 6, 2018

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ..... A01H 5/08; A01H 6/88
See application file for complete search history.

*Primary Examiner* — Annette H Para
(74) *Attorney, Agent, or Firm* — Baker Manock & Jensen, PC; Eric C. Cole

(57) ABSTRACT

A new and distinct variety of grapevine plant named 'SV30-14-12' particularly characterized by its ellipsoidal shaped, dark red to reddish black berries which are very large, sweet and have crisp texture. Productivity is very high with shoots producing one or two clusters on spur pruned vines. Flower clusters generally require some hand thinning to produce clusters which are not overly compact.

2 Drawing Sheets

Latin name of the genus and species of the plant claimed: The plant claimed relates to a new and distinct variety of *Vitis vinifera*.

Variety denomination: The plant claimed shall be known as 'SV30-14-12'.

CROSS REFERENCES TO RELATED APPLICATIONS

The present application claims the benefit of Provisional Application No. 62/708,982 filed Dec. 28, 2017, which is incorporated herein by reference.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV30-14-12'. As used herein, 'grapevine' refers to all plant parts including, vines, canes, tendrils, leaves, fruit and roots of grapevine named 'SV30-14-12'. Grapevine named 'SV30-14-12' is the result of an effort to produce a red, seedless table grape with fruit characteristics superior to currently available red skinned grape cultivar 'Scarlet Royal' (U.S. Plant Pat. No. 16,229). This new cultivar originated from a cross conducted in May 2009 near McFarland, Calif. between grapevine plant selection 'SV16-72-83'(unpatented) and pollen parent 'SV21-66-158' (U.S. Plant Pat. No. 24,510). Resultant ovules from the cross were harvested 42 days after pollination and cultured on 'McCown's Woody Plant Medium' at a temperature of 22° C. for twelve weeks. Subsequently, the resultant embryonic plants were cultured in the same medium in the laboratory under twelve hours of light from standard fluorescent lamps at 26.4° C. The seedlings from this effort were transplanted to the greenhouse in October of 2010 and grown in the greenhouse at 26.4° C. with 12 hours' illumination under high pressure sodium vapor lamps. The seedling population of 315 plants was planted in the field in the spring of 2010 near Delano, Calif. The new grapevine was selected from this seedling population on Aug. 8, 2011. It was then propagated by cuttings and bench grafted to 'Freedom' (unpatented) rootstock in 2012. The present invention has been found to retain its distinctive characteristics through two successive asexual propagations.

Grapevine named 'SV30-14-12' differs from the female parent grapevine 'SV16-72-83' (unpatented) in that grapevine named 'SV30-14-12' has ellipsoidal shaped, dark red to black skinned, seedless berries, whereas 'SV16-72-83' has ovate shaped, black skinned berries with partially lignified seed traces.

Grapevine named 'SV30-14-12' differs from its male parent, 'SV21-66-158' (U.S. Plant Pat. No. 24,510) in that grapevine named 'SV30-14-12' has dark red to black skinned berries while 'SV21-66-158' (U.S. Plant Pat. No. 24,510) had green skinned berries.

Grapevine named 'SV30-14-12' differs from the commercial cultivar 'Scarlet Royal' (U.S. Plant Pat. No. 16,229) in that grapevine named 'SV30-14-12' has compact clusters requiring some hand thinning while 'Scarlet Royal' (U.S. Plant Pat. No. 16,229) clusters are less compact. Grapevine named 'SV30-14-12' produces berries with no astringent flavour whereas 'Scarlet Royal' (U.S. Plant Pat. No. 16,229) produces berries at full ripeness which are astringent. Additionally, grapevine named 'SV30-14-12' responds very well to applications of sizing gibberellic acid, producing berries which exceed 10 g in mass.

SUMMARY OF THE INVENTION

The following are the most outstanding and distinguishing characteristics of the ripe fruit of this new variety when grown under normal horticultural practices near McFarland, Calif. Some of the characteristics may vary depending upon changes in crop load and change of location of cultivation.

1. Dark red to black skinned fruit;
2. Very firm berry texture; and
3. Very large, ellipsoidal shaped berries with sweet taste.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken in 2016 from a plant about 5 years-old, grown in a field near McFarland, Calif.

DETAILED BOTANICAL DESCRIPTION

Figure 1:
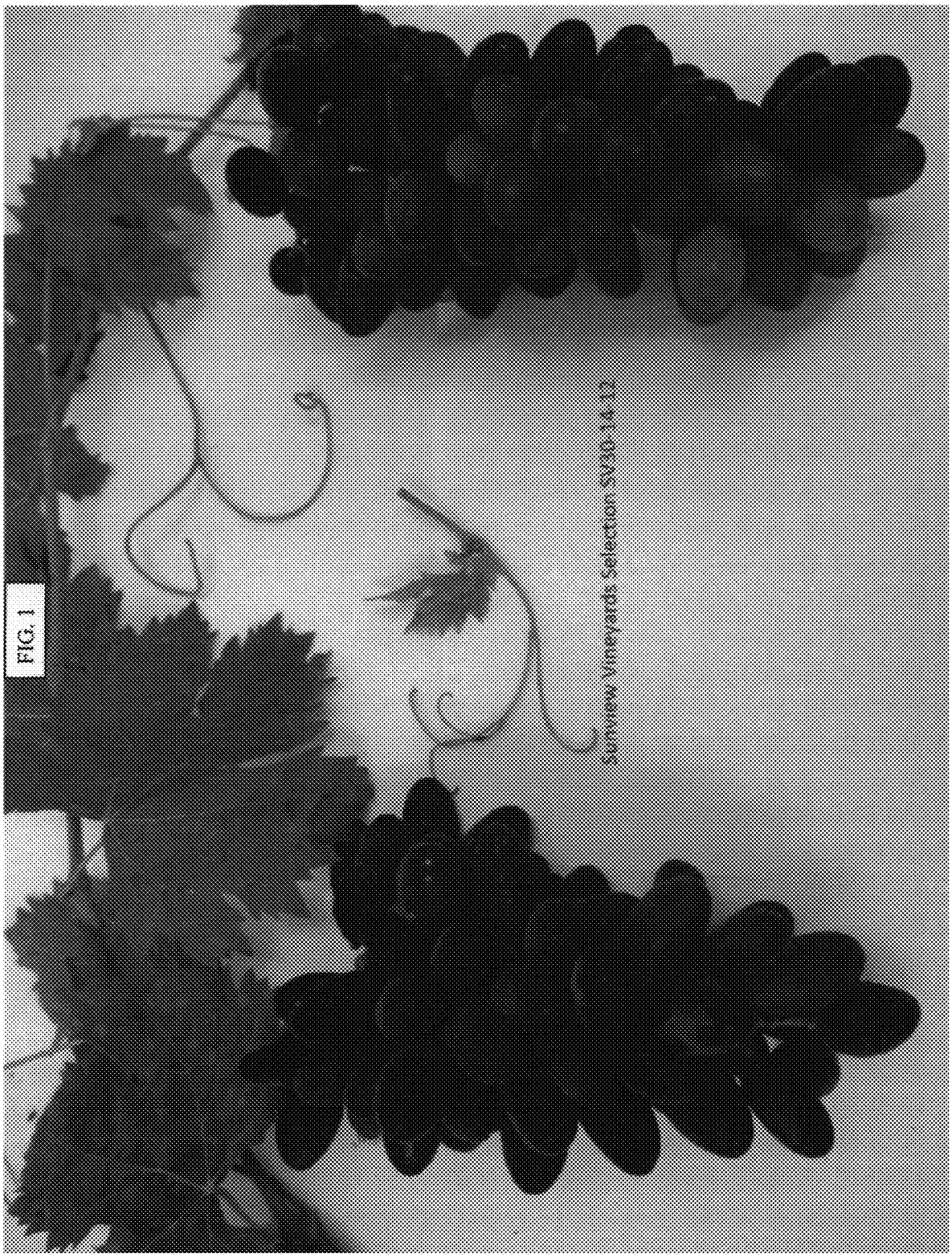
FIG. 1 Natural fruit cluster and cluster sprayed with gibberellic acid with shoots, leaves, tendrils and shoot tips.
Figure 2:
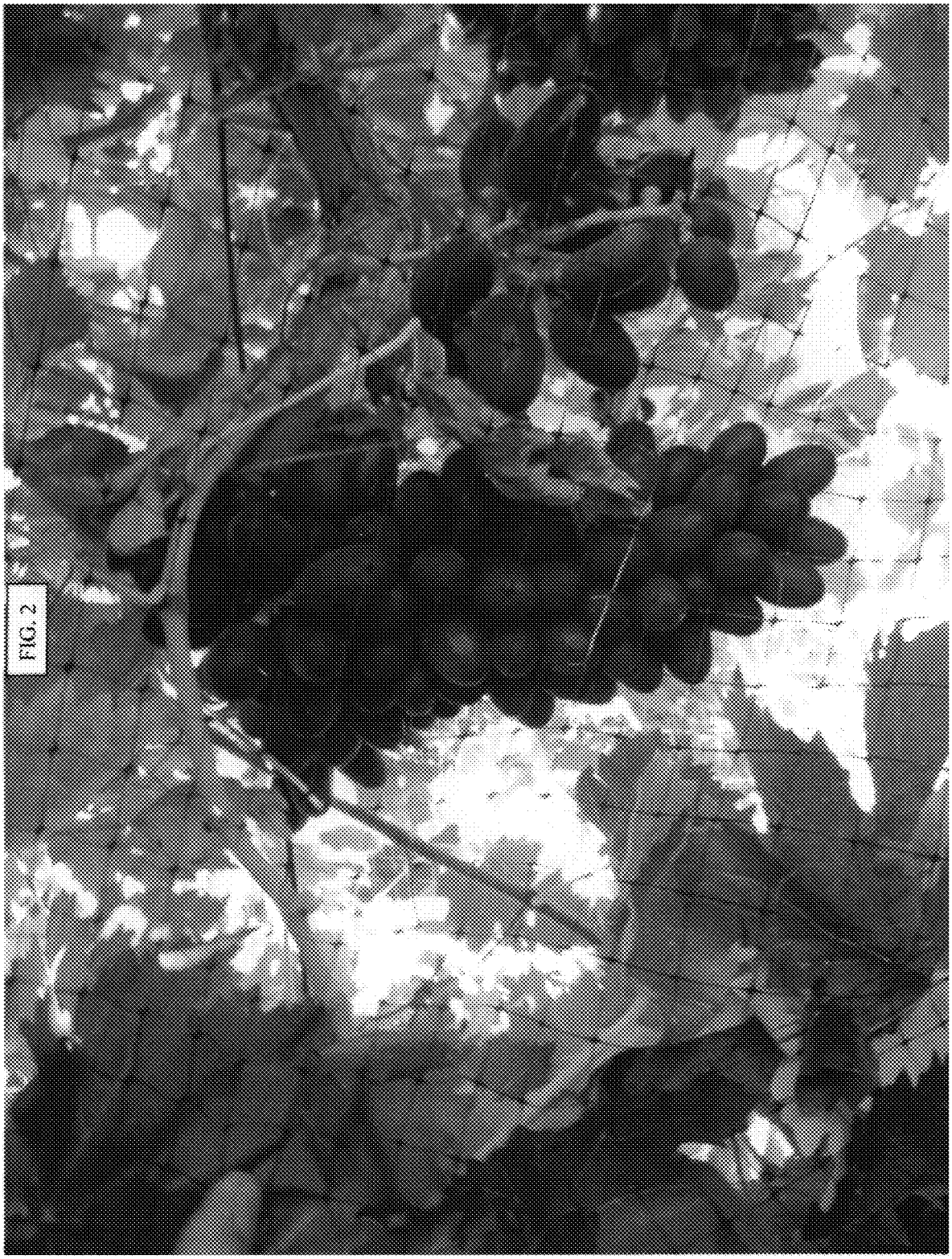
FIG. 2 Fruit clusters on vine sprayed with gibberellic acid and trunk girdled.

The following detailed description sets forth the distinctive characteristics of 'SV30-14-12'. Descriptions of the new invention apply to vines of grapevine named 'SV30-14-12' grown on 'Freedom' rootstock at a density of 1,537 vines per hectare grown near McFarland, Calif. in 2017. These vines were in their fifth year of full production, having been planted in 2012. These descriptions are believed to apply generally to the new variety grown under similar circumstances elsewhere. References to color correspond to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office Interantional de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:
- *Family*.—Vitaceae.
- *Botanical name*.—*Vitis vinifera*.
- *Variety name*.—'SV30-14-12'.

Plant:
- *Vigor*.—Medium; vines spur-pruned and shoot thinned to 32 shoots.
- *Density of foliage*.—Moderate.
- *Productivity*.—Very productive when spur pruned, up to 32,000 kg/hectare.
- *Hardiness*.—Hardiness observed to 0° C.
- *Rootstock*.—'Freedom' (unpatented).

Trunk:
- *Shape*.—Broadly elliptical.
- *Straps*.—Long, split.
- *Surface texture*.—Shaggy.
- *Trunk circumference*.—24.6 cm at 1.0 m of height.
- *Inner bark color*.—RHS Greyed orange group 174C.
- *Outer bark color*.—RHS Brown group N200B.

Mature leaves:
- *Average blade length*.—15.2 cm.
- *Average blade width*.—18.6 cm.
- *Size of blade*.—Large.
- *Shape*.—Pentagonal.
- *Anthocyanin coloration of main veins on the upper side of the blade*.—Absent.
- *Mature leaf profile*.—Undulating, cupped upwards and flattened within plane of blade.
- *Blistering* (*upper surface*).—Absent.
- *Leaf blade tip*.—In plane of blade.
- *Margins*.—Lobed, serrated, undulating.
- *Apex*.—Narrowly acute.
- *Bases*.—Sagittate.
- *Thickness*.—Medium.
- *Undulation of blade between main and lateral veins*.—Slight.
- *Shape of teeth*.—Broadly conical, both sides convex.
- *Length of teeth*.—3-9 mm.
- *Ratio length/width of teeth*.—About 1:1.
- *General shape of petiole sinus*.—Half open.
- *Tooth at petiole sinus*.—Absent.
- *Petiole sinus limited by veins*.—Absent.
- *Shape of upper lateral sinus*.—Closed.
- *Prostrate hairs between veins* (*lower surface*).—Absent.
- *Erect hairs between veins* (*lower surface*).—Absent.
- *Prostrate hairs on main veins* (*lower surface*).—Absent.
- *Density of erect hairs on main veins* (*lower surface*).—Moderate, limited to junctions of main veins.
- *Prostrate hairs on main veins* (*upper surface*).—Absent.
- *Upper surface*.—Summer color: RHS Green group 137A. Surface texture: Smooth. Surface appearance: Dull. Goffering of blade: Absent.
- *Lower surface*.—Summer color: RHS Green group 138A. Anthocyanin coloration of main veins on lower leaf surface: Absent. Anthocyanin coloration on laterals: No. Glossiness: Low. Pubescence: Absent. Surface texture: Rough. Surface appearance: Dull.
- *Petiole*.—Length: 11.8 cm. Length of petiole compared to middle vein: Slightly shorter. Density of prostrate hairs: Absent. Density of erect hairs: Absent. Shape of base of petiole sinus: Half open.
- *Color*.—RHS Yellow green group 144C.

Tendrils:
- *Color*.—In shade: RHS Yellow green group 150B. In sun: RHS Yellow green group 144B.

Growing tips (young shoot):
- *Pubescence*.—Sparse, prostrate.
- *Color*.—RHS Yellow Green Group 144C.
- *Anthocyanins*.—Absent.
- *Shape*.—Flattened.
- *Apex*.—Open.
- *Shoot attitude*.—Semi-erect.

Flowers:
- *Flower sex*.—Perfect.
- *Position of first flowering nodes*.—Usually on node 4.
- *Number of inflorescences per shoot*.—One or two on nodes 4 and 5. Date of full bloom: May 6th.

Fruit:
- *Ripening period*.—Mid-season.
- *Date of ripening*.—August 29th at McFarland, Calif.
- *Particular flavor*.—Neutral *Vitis vinifera*.
- *Use*.—Fresh market.
- *Keeping quality*.—Good.
- *Shipping quality*.—Good.
- *Date of first harvest*.—August 29th.

*Solids-sugar.*—17 brix at full maturity.

*Refractometer test.*—17.0 brix.

*Bunch.*—Size: Medium. Length (peduncle excluded): 23.5 cm. Width: 13.5 cm. Weight: Natural, without gibberellic acid treatment: 541 g. Density: Well-filled to compact. Number of berries: 61. Form: Cylindrical with no pronounced shoulder.

*Peduncle.*—Length: 3.2 cm. Lignification: Medium. Color: RHS Yellow green group 144B.

*Berry.*—Size: Large. Uniformity of size: Uniform. Weight. Natural, without gibberellic acid treatment: About 8.7 g. Shape: Ellipsoidal. Presence of seeds: Seedless; most berries develop one or two tiny ovule traces less than 1 mm in length. Cross section: Circular. Dimensions: Longitudinal axis: About 3.0 cm. Horizontal axis: About 2.0 cm. Skin color (without bloom): RHS Red Purple Group 61B to black where exposed to direct sunlight. Juiciness of flesh: Very juicy. Berry firmness: Very firm. Particular flavor: Neutral, typical *vinifera*. Bloom (cuticular wax): Heavy. Pedicel length: About 8.7 mm. Berry separation from pedicel: Moderately easy.

*Skin.*—Thickness: Medium. Texture: Tender. Reticulation: Absent. Roughness: Absent. Tenacity: Tenacious to flesh. Tendency to crack: Resistant.

Disease and insect resistance: Moderately susceptible to powdery mildew which may be controlled with standard fungicides in California.

Having thus described and illustrated our new variety of grapevine, I claim:

1. A new and distinct variety of grapevine plant named 'SV30-14-12', and parts thereof, substantially as illustrated and described herein.

* * * * *